US00PP23672P2

(12) United States Plant Patent
Lannes

(10) Patent No.: US PP23,672 P2
(45) Date of Patent: Jun. 18, 2013

(54) ***MANDEVILLA* PLANT NAMED 'LANARIZONA'**

(50) Latin Name: *Mandevilla hybrida*
Varietal Denomination: Lanarizona

(75) Inventor: Robert Lannes, Malause (FR)

(73) Assignee: D.H.M. Innovation S.A.S., Malause (FR)

( * ) Notice: Subject to any disclaimer, the term of this patent is extended or adjusted under 35 U.S.C. 154(b) by 0 days.

(21) Appl. No.: 13/374,929

(22) Filed: Jan. 23, 2012

(51) Int. Cl.
*A01H 5/00* (2006.01)

(52) U.S. Cl.
USPC ..... Plt./232

(58) Field of Classification Search
USPC ..... Plt./232
See application file for complete search history.

(56) References Cited

PUBLICATIONS

Pluto Plant Variety Database 2012-05 search for Lanarizona.*

* cited by examiner

*Primary Examiner* — Annette Para
(74) *Attorney, Agent, or Firm* — C. A. Whealy

(57) ABSTRACT

A new and distinct cultivar of *Mandevilla* plant named 'Lanarizona', characterized by its upright and vining plant habit; vigorous growth habit; large glossy dark green-colored leaves; early and freely flowering habit; and large white-colored flowers.

2 Drawing Sheets

Botanical designation: *Mandevilla hybrida.*
Cultivar denomination: 'LANARIZONA'.

BACKGROUND OF THE INVENTION

The present invention relates to a new and distinct cultivar of *Mandevilla* plant, botanically known as *Mandevilla hybrida* and hereinafter referred to by the name 'Lanarizona'.

The new *Mandevilla* plant is a product of a planned breeding program conducted by the Inventor in Malause, France. The objective of the breeding program is to create new uniform and early-flowering *Mandevilla* plants with numerous attractive flowers.

The new *Mandevilla* plant originated from a cross-pollination conducted by the Inventor in Malause, France on Jul. 14, 2005 of (*Mandevilla*×*amabilis*)×*Mandevilla splendens* 'PSJAM DP1', disclosed in U.S. Plant Pat. No. 10,413, as the female, or seed parent with *Mandevilla Sanderi* 'Blanc', not patented, as the male, or pollen, parent. The new *Mandevilla* plant was discovered and selected by the Inventor as a single flowering plant from within the progeny of the stated cross-pollination in a controlled greenhouse environment in Malause, France in November, 2007.

Asexual reproduction of the new *Mandevilla* plant by cuttings in a controlled greenhouse environment in Malause, France, since May, 2010 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Lanarizona'. These characteristics in combination distinguish 'Lanarizona' as a new and distinct *Mandevilla* plant:

1. Upright and vining plant habit.
2. Vigorous growth habit.
3. Large glossy dark green-colored leaves.
4. Early and freely flowering habit.
5. Large round white-colored flowers.

Plants of the new *Mandevilla* can be compared to plants of the female parent, 'PSJAM DP1'. Plants of the new *Mandevilla* differ primarily from plants of 'PSJAM DP 1' in the following characteristics:

1. Plants of the new *Mandevilla* have larger and flatter leaves than plants of 'PSJAM DP1'.
2. Plants of the new *Mandevilla* have larger flowers than plants of 'PSJAM DP1'.
3. Plants of the new *Mandevilla* and 'PSJAM DP1' differ in flower color as plants of 'PSJAM DP1' have deep pink-colored flowers.

Plants of the new *Mandevilla* can be compared to plants of the male parent, 'Blanc'. Plants of the new *Mandevilla* differ primarily from plants of 'Blanc' in the following characteristics:

1. Plants of the new *Mandevilla* are more vigorous than plants of 'Blanc'.
2. Plants of the new *Mandevilla* have larger and darker green-colored leaves than plants of 'Blanc'.
3. Plants of the new *Mandevilla* have larger flowers than plants of 'Blanc'.

Plants of the new *Mandevilla* can be compared to plants of selections of *Mandevilla*×*amabilis* known to the Inventor, not patented. In side-by-side comparisons conducted in Malause, France, plants of the new *Mandevilla* differed from plants of selections of *Mandevilla*×*amabilis* known to the Inventor in the following characteristics:

1. Plants of the new *Mandevilla* had larger, flatter and darker green-colored leaves than plants of selections of *Mandevilla×amabilis* known to the Inventor.
2. Plants of the new *Mandevilla* flowered about two weeks earlier than plants of selections of *Mandevilla×amabilis* known to the Inventor.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lanarizona' grown in a container.

The photograph on the second sheet is a close-up view of a typical flowering plant of 'Lanarizona'.

DETAILED BOTANICAL DESCRIPTION

The aforementioned photographs and following observations, measurements and values describe plants grown during the autumn in 27-cm containers in polyethylene-covered greenhouse in Malause, France and under cultural practices typical of *Mandevilla* commercial production. During the production of the plants, day temperatures ranged from 8° C. to 26° C. and night temperatures ranged from 3° C. to 15° C. Plants were one year old when the photographs and description were taken. In the following description, color references are made to The Royal Horticultural Society Colour Chart, 2007 Edition, except where general terms of ordinary dictionary significance are used.

Botanical classification: *Mandevilla hybrida* 'Lanarizona'.

Parentage:

*Female, or seed, parent*.—(*Mandevilla×amabilis*)× *Mandevilla splendens* 'PSJAM DP1', disclosed in U.S. Plant Pat. No. 10,413.

*Male, or pollen, parent*.—*Mandevilla Sanderi* 'Blanc', not patented.

Propagation:

*Type*.—By vegetative cuttings.

*Time to initiate roots, summer*.—About two weeks at 23° C. to 25° C.

*Time to initiate roots, winter*.—About three weeks at 23° C. to 25° C.

*Time to produce a rooted young plant, summer*.—About five to six weeks at 23° C. to 25° C.

*Time to produce a rooted young plant, winter*.—About six to eight weeks at 23° C. to 25° C.

*Root description*.—Fibrous, fine; light yellowish white in color.

*Rooting habit*.—Freely branching; medium density.

Plant description:

*Plant and growth habit*.—Upright and vining plant habit; columnar in shape; vigorous growth habit.

*Plant height*.—About 118.5 cm.

*Plant diameter* (*spread*).—About 89 cm.

*Lateral branch description*.—Branching habit: Freely branching habit with about twelve lateral branches developing per plant; pinching enhances lateral branch development. Length: About 50.4 cm. Diameter: About 3 mm. Internode length: About 7.7 cm. Strength: Strong. Texture: Slightly scabrous, glabrous. Color: Close to 143C.

Foliage description:

*Arrangement*.—Opposite, simple.

*Length*.—About 11.7 cm.

*Width*.—About 6.7 cm.

*Shape*.—Oblong to broadly obovate.

*Apex*.—Abruptly acute.

*Base*.—Truncate.

*Margin*.—Entire.

*Texture, upper and lower surfaces*.—Smooth, glabrous; glossy.

*Venation pattern*.—Pinnate, reticulate.

*Color*.—Developing leaves, upper surface: Darker and more intense than 143A. Developing leaves, lower surface: Between 143B and 146A. Fully expanded leaves, upper surface: Darker than between N137A and 147A; venation, close to 143B. Fully expanded leaves, lower surface: Close to 147B; venation, close to 145D.

*Petiole length*.—About 1.5 cm.

*Petiole diameter*.—About 2.5 mm.

*Petiole texture, upper and lower surfaces*.—Smooth, glabrous.

*Petiole color, upper and lower surfaces*.—Close to 144B to 144C.

Flower description:

*Flower type and flowering habit*.—Single salverform flowers arranged in axillary racemes; flowers rounded and face upright and outwardly; freely flowering habit with about eleven flowers developing per inflorescence and about 130 flowers developing per plant.

*Natural flowering season*.—Early flowering habit with plants begin to flower about six weeks after planting; plants flower continuously from summer into the autumn in France.

*Flower longevity on the plant*.—About seven days; flowers not persistent.

*Fragrance*.—None detected.

*Flowers*.—Appearance: Flared trumpet, corolla fused and five-parted. Diameter: About 10.3 cm. Depth (length): About 6 cm. Tube length: About 5 cm.

*Flower buds*.—Length: About 4.9 cm. Diameter: About 8 mm. Shape: Narrowly obovate. Color: Close to 144D; towards the base, close to 144B.

*Corolla*.—Quantity and arrangement: Five petals arranged in a single whorl and fused at the base. Petal length: About 9.3 cm. Petal width: About 5.3 cm. Petal shape and appearance: Roughly spatulate; lower 55% of the petal is fused; upper free portions are slightly reflexed. Petal apex: Rounded to bluntly acute. Petal margin: Entire. Petal texture, upper and lower surfaces: Smooth, glabrous; slightly velvety. Throat texture: Smooth, glabrous. Tube texture: Smooth, glabrous. Color: Petal, when opening, upper surface: Close to N155B; very slightly flushed with close to 69D; throat, close to 14B to 17A, towards the base of the throat, close to 145A. Petal, when opening, lower surface: Close to N155B; tube, between 157D and 160D, towards the base of the tube, close to 145A. Petal, fully opened, upper surface: Close to N155B; throat, close to 13A to 17A, towards the base of the throat, close to 145B. Petal, fully opened, lower surface: Close to N155B; tube, close to 158D, towards the base of the tube, close to 145C.

*Corona*.—Quantity and arrangement: Five sepals arranged in a single whorl. Sepal length: About 7 mm. Sepal width: About 2 mm. Sepal shape: Lanceolate. Sepal apex: Narrowly acuminate. Sepal base: Roughly truncate. Sepal margin: Entire. Sepal texture, upper and lower surfaces: Smooth, glabrous. Sepal color: Immature and mature, upper surface: Close to 144C; towards the base, close to 144B. Immature and mature, lower surface: Close to 144C; towards the base, close to 144B.

*Peduncles*.—Length: About 7.2 cm. Diameter: About 2 mm. Texture: Smooth, glabrous. Strength: Flexible, but strong. Color: Close to 144B.

*Pedicels*.—Length: About 1.5 cm. Diameter: About 1.5 mm. Texture: Smooth, glabrous. Strength: Flexible, but strong. Color: Close to 144B.

*Reproductive organs*.—Stamens: Quantity and arrangement: Typically five; basifixed; anthers connivent. Filament length: About 1 mm. Anther shape: Ellipsoidal. Anther length: About 7 mm. Anther color: Close to 161D. Pollen amount: None observed. Pistils: Quantity: Typically one. Pistil length: About 2.3 cm. Style length: About 2 cm. Style color: Close to 144D. Stigma shape: Conical. Stigma color: Close to 145D. Ovary color: Close to 144C.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be hardy to USDA Hardiness Zone 9.

It is claimed:

1. A new and distinct *Mandevilla* plant named 'Lanarizona' as illustrated and described.

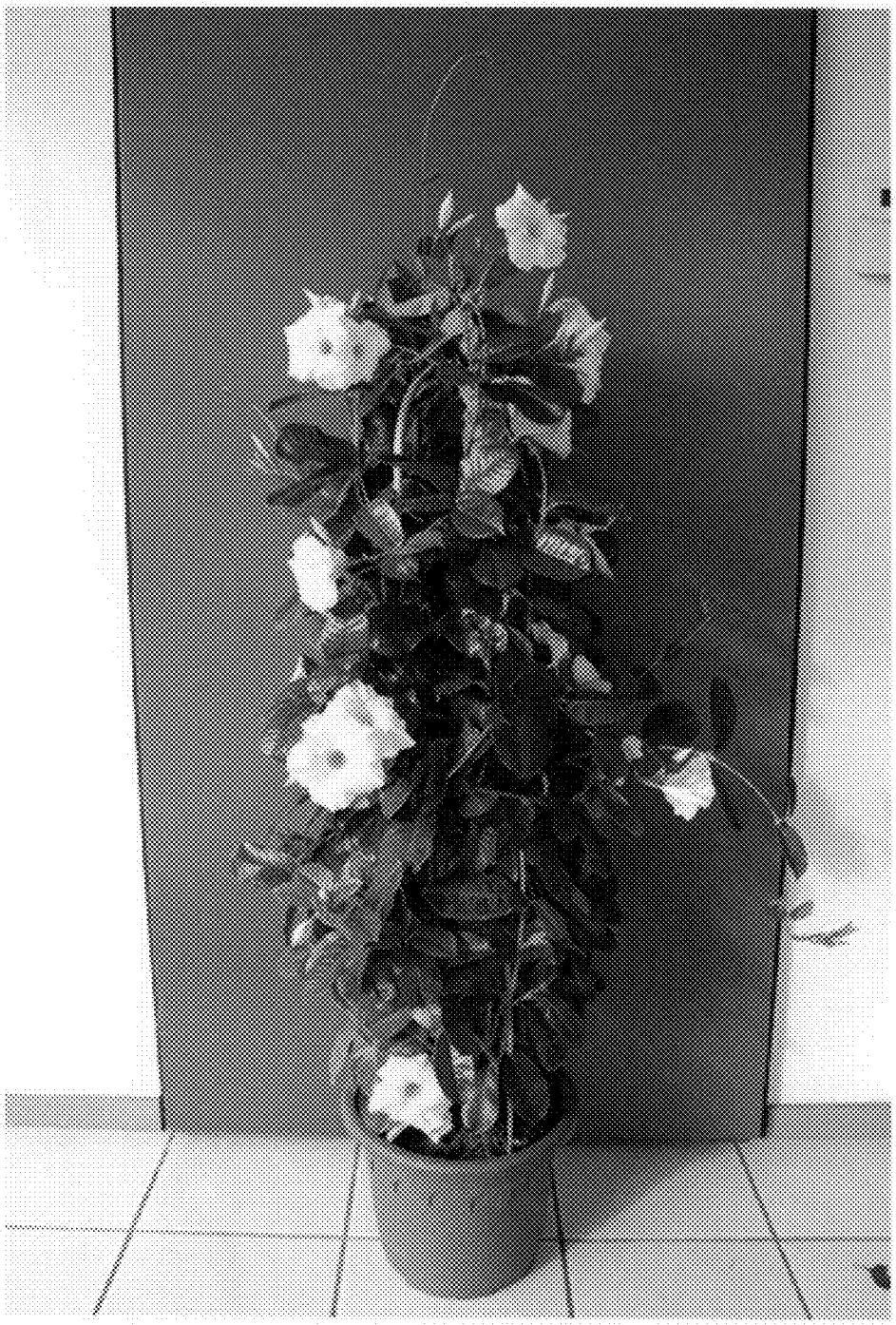

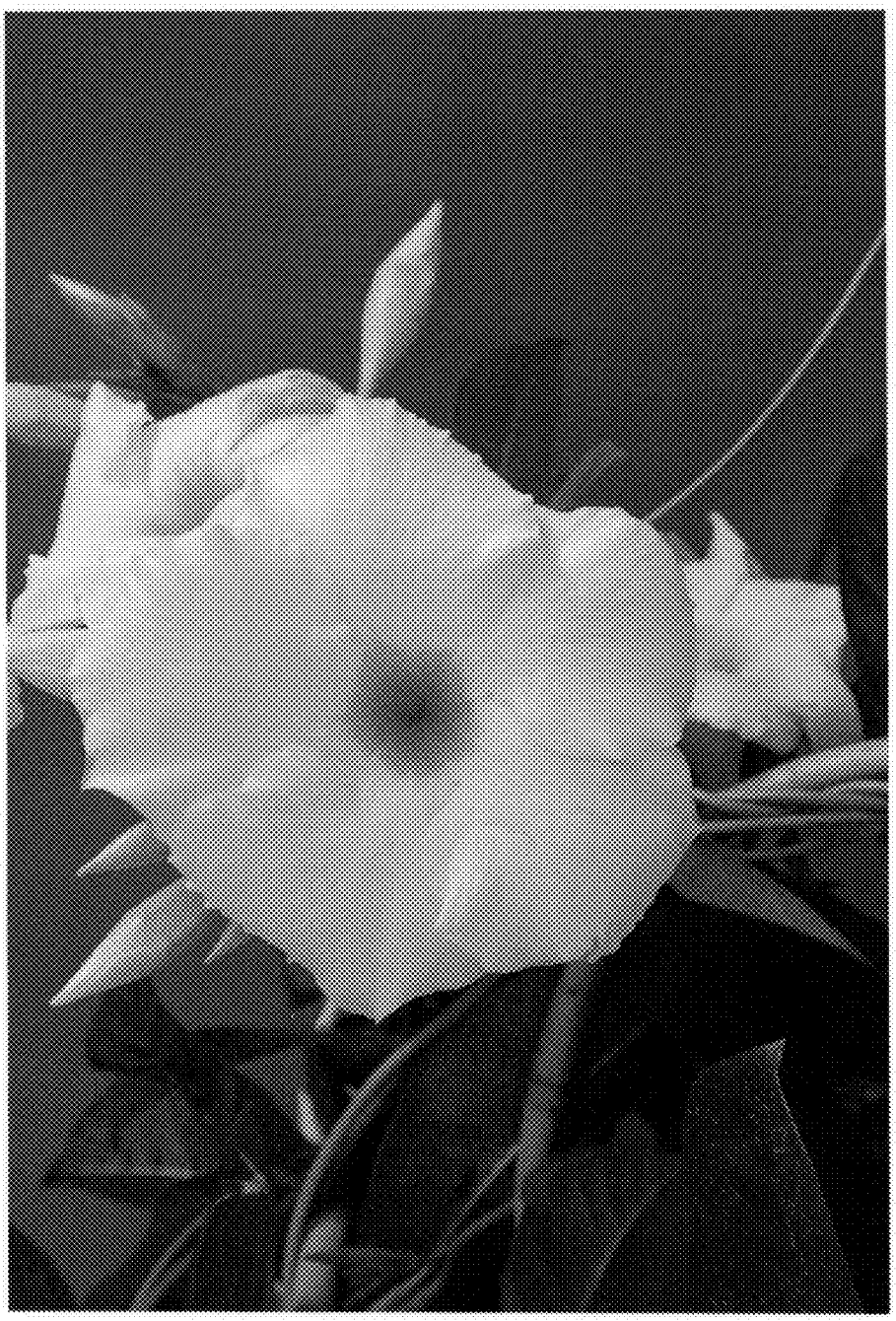

* * * * *